(12) United States Patent
Park et al.

(10) Patent No.: US 10,792,340 B2
(45) Date of Patent: *Oct. 6, 2020

(54) ANTIBACTERIAL COMPOSITION FOR COMBATING CARBAPENEM-RESISTANT GRAM-NEGATIVE BACTERIA COMPRISING ADK PROTEIN AS ACTIVE INGREDIENT

(71) Applicant: KONKUK UNIVERSITY GLOCAL INDUSTRY-ACADEMIC COLLABORATION FOUNDATION, Chungju-si, Chungcheongbuk-do (KR)

(72) Inventors: Yeong Min Park, Seoul (KR); In Duk Jung, Cheongju-si (KR); Seung Jun Lee, Yeongju-si (KR)

(73) Assignee: KONKUK UNIVERSITY GLOCAL INDUSTRY-ACADEMIC COLLABORATION FOUNDATION, Chungju-si, Chungcheon (KR)

( * ) Notice: Subject to any disclaimer, the term of this patent is extended or adjusted under 35 U.S.C. 154(b) by 84 days.

This patent is subject to a terminal disclaimer.

(21) Appl. No.: 15/563,795

(22) PCT Filed: Apr. 4, 2016

(86) PCT No.: PCT/KR2016/003467
§ 371 (c)(1),
(2) Date: Oct. 2, 2017

(87) PCT Pub. No.: WO2016/159741
PCT Pub. Date: Oct. 6, 2016

(65) Prior Publication Data
US 2018/0078619 A1    Mar. 22, 2018

(30) Foreign Application Priority Data

Apr. 3, 2015   (KR) .................. 10-2015-0047360

(51) Int. Cl.
| | | |
|---|---|---|
| *A61K 38/45* | (2006.01) | |
| *A61K 35/66* | (2015.01) | |
| *A61K 8/98* | (2006.01) | |
| *A61P 31/04* | (2006.01) | |
| *A01N 63/10* | (2020.01) | |
| *A23L 33/17* | (2016.01) | |

(52) U.S. Cl.
CPC .............. *A61K 38/45* (2013.01); *A01N 63/10* (2020.01); *A23L 33/17* (2016.08); *A61K 8/98* (2013.01); *A61K 35/66* (2013.01); *A61P 31/04* (2018.01); *C12Y 207/04003* (2013.01); *A23V 2002/00* (2013.01); *Y02A 50/473* (2018.01)

(58) Field of Classification Search
CPC .......... A61K 38/45; A61K 35/66; A61K 8/98; C12Y 207/04003; A23L 33/17; A23L 33/195; A23V 2002/00; A23V 2250/70; A23V 2250/156; Y02A 50/473; A61P 31/04; A01N 63/02; A23K 20/147
See application file for complete search history.

(56) References Cited

U.S. PATENT DOCUMENTS

| | | | |
|---|---|---|---|
| 5,856,160 A * | 1/1999 | Hillman ............... | C12N 9/1229 435/194 |
| 10,543,258 B2 * | 1/2020 | Park ....................... | A61K 38/16 |
| 2010/0035232 A1 * | 2/2010 | Ecker .................. | A61K 31/4741 435/5 |
| 2010/0129391 A1 * | 5/2010 | Reed ....................... | A61K 39/04 424/190.1 |
| 2012/0232040 A1 * | 9/2012 | Chen ....................... | A61K 31/12 514/154 |
| 2016/0263199 A1 * | 9/2016 | Park ....................... | A61K 38/45 |
| 2019/0083581 A1 * | 3/2019 | Park ....................... | A61K 38/16 |

FOREIGN PATENT DOCUMENTS

| | | |
|---|---|---|
| KR | 10-2012-0004448 A | 1/2012 |
| KR | 10-2013-0129326 A | 11/2013 |
| KR | 10-2014-0039449 A | 4/2014 |
| KR | 101477795 B1 * | 1/2015 |
| WO | 2014/026143 A1 | 2/2014 |
| WO | 2014/134701 A1 | 9/2014 |

OTHER PUBLICATIONS

Fu, LM et al. Is *Mycobacterium tuberculosis* a closer relative to Gram-positive or Gram-negative bacterial pathogens? Tuberculosis. 2002. 82(2/3): 85-90. (Year: 2002).*

* cited by examiner

*Primary Examiner* — Renee Claytor
*Assistant Examiner* — Susan E. Fernandez
(74) *Attorney, Agent, or Firm* — Vorys, Sater, Seymour & Pease LLP; Mih Suhn Koh

(57) ABSTRACT

Provided is an antibacterial composition against carbapenem-resistant gram-negative bacteria which includes, as an active ingredient, adenylate kinase (ADK) protein derived from *Mycobacterium tuberculosis*. The ADK protein derived from *Mycobacterium tuberculosis*, according to the subject matter, has excellent antimicrobial activity against carbapenem-resistant gram-negative bacteria, and thus may be usefully used in a variety of fields as an antibacterial composition.

8 Claims, 1 Drawing Sheet
Specification includes a Sequence Listing.

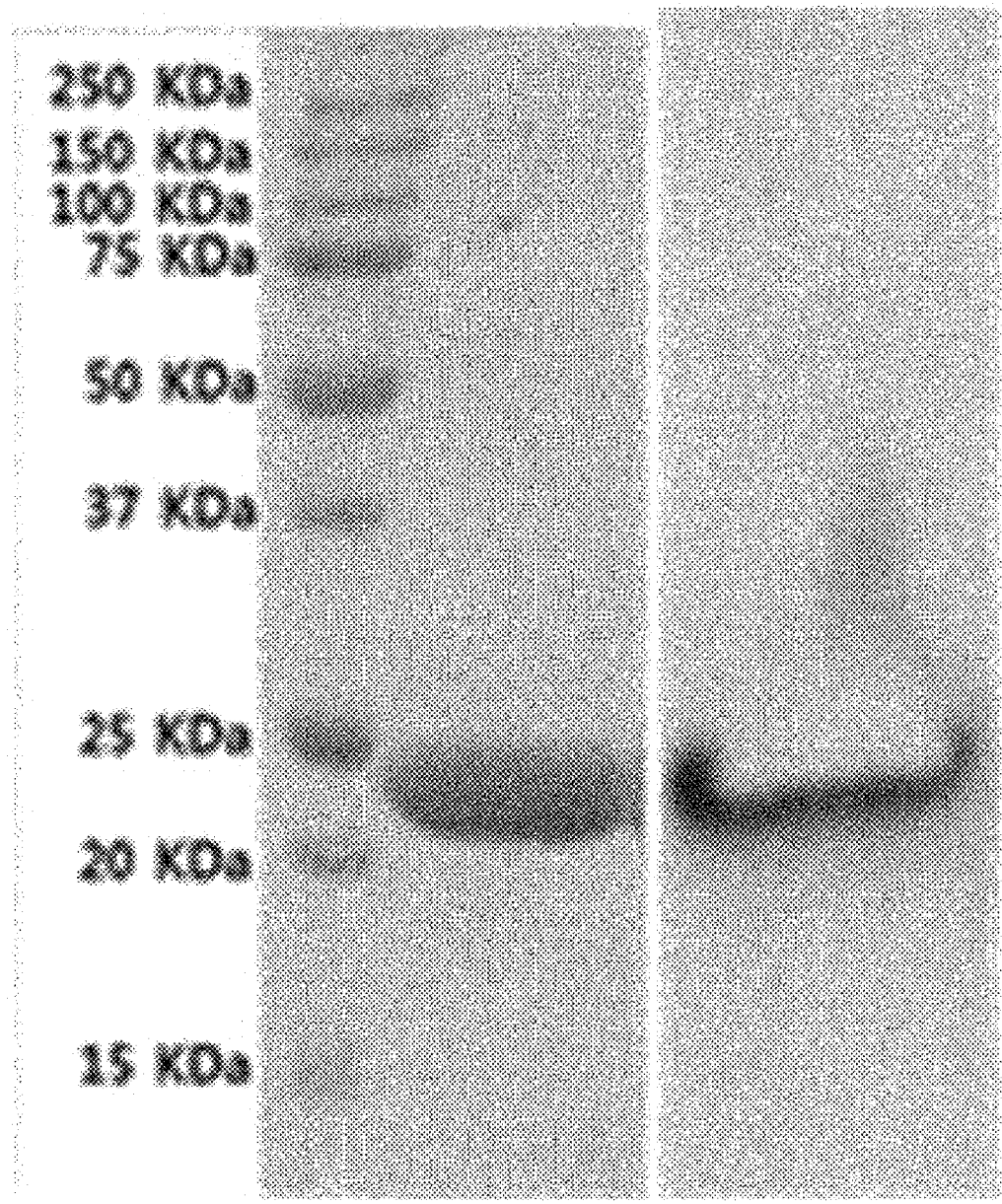

ANTIBACTERIAL COMPOSITION FOR COMBATING CARBAPENEM-RESISTANT GRAM-NEGATIVE BACTERIA COMPRISING ADK PROTEIN AS ACTIVE INGREDIENT

STATEMENT REGARDING GOVERNMENT RIGHTS

The present invention was undertaken with the support of 1) Functional analysis of PADK as therapeutic drugs for Polymicrobial sepsis and Carbapenem-resistance Gram-negative bacterial sepsis No. 2015R1A2A1A13001713 grant funded by the National Research Foundation of Korea, 2) Laboratory of Integrated Immunoregulation (LII) No. 2013R1A4A1069575 grant funded by the National Research Foundation of Korea.

CROSS-REFERENCE TO RELATED APPLICATION

This application claims priority to and the benefit of Korean Patent Application No. 10-2015-0047360 filed on Apr. 3, 2015 and International Patent Application No. PCT/KR2016/003467, filed on Apr. 4, 2016, the disclosure of which is incorporated herein by reference in its entirety.

SEQUENCE LISTING

The Sequence Listing submitted in text format (.txt) filed on Oct. 2, 2017, named "SequenceListing.txt", created on Sep. 22, 2017, 3.00 KB), is incorporated herein by reference.

TECHNICAL FIELD

The present invention relates to an antibacterial composition against carbapenem-resistant gram-negative bacteria which includes, as an active ingredient, adenylate kinase (ADK) protein derived from *Mycobacterium tuberculosis*.

BACKGROUND ART

Generally, antibacterial agents collectively refer to antimicrobial agents, in particular, substances having an antimicrobial effect, in particular, substances having an excellent antimicrobial effect through inhibition of systems in which bacteria synthesize cell walls, proteins, or the like, or agents prepared therefrom. Major ingredients of antibacterial agents are extracted mainly from fungi, and such antibacterial agents are widely used these days to treat diseases caused by bacterial infection, and the like.

Starting with the discovery of penicillin antibiotics by Fleming in the 20$^{th}$ century, numerous antimicrobial agents and antibiotics have been developed to escape from diseases caused by bacterial infections. Such antibacterial agents occupy an essential position in our lives, and are widely used in a variety of applications such as drugs, foods, cosmetic preservatives, and the like. However, in the case of antibacterial agents using chemical synthetic materials, the number of bacteria having resistance thereto gradually increases, and, accordingly, the use thereof is increasingly limited.

Antimicrobial-resistant bacteria refer to bacteria that are resistant to certain antimicrobial agents and thus do not respond thereto. For example, penicillin-resistant *Staphylococcus aureus* that does not respond to penicillin belongs to these bacteria. In addition, methicillin-resistant *Staphylococcus aureus* (MRSA), which was first reported in the academic world in 1961 and since then, has become a major pathogenic infectious bacterium globally, and vancomycin resistant *enterococcus* (VRE), which has resistance to vancomycin, first discovered in Europe in 1988, are known, and in the late 1990s, vancomycin intermediate-resistant *Staphylococcus aureus* (VISA) was reported in Japan, the U.S.A., France, and Korea. In addition, vancomycin-resistant *Staphylococcus aureus* (VRSA), wherein vancomycin is known as the last therapeutic agent of *Staphylococcus aureus* which is the most common causative bacterium of human infection, was first reported globally in 2002 by the Centers for Disease Control, and thus the possibility of proliferation of so-called super bacteria is greatly increasing.

Meanwhile, β-lactam antibiotics, considered most importantly in the antibiotics field, include penam antibiotics commonly known as penicillin, cefem antibiotics commonly known as cephalosporin, penem antibiotics, and carbapenem antibiotics. Among these, examples of carbapenem antibiotics include imipenem, panipenem, meropenem, ertapenem, and the like, which are commercially available.

Therefore, the inventors of the present invention made an effort to develop of novel antimicrobial agents and, as a result, verified that adenylate kinase or adenosine kinase (ADK) protein derived from *Mycobacterium tuberculosis* exhibited excellent antimicrobial activity against carbapenem-resistant gram-negative bacteria, thus completing the present invention.

DISCLOSURE

Technical Problem

An object of the present invention is to provide an antibacterial composition against carbapenem-resistant gram-negative bacteria which includes ADK protein as an active ingredient.

Another object of the present invention is to provide a composition for the prevention or treatment of infectious diseases caused by carbapenem-resistant gram-negative bacteria, the composition including ADK protein as an active ingredient.

Technical Solution

The prevent invention provides an antibacterial composition, a quasi-drug, a food additive, or a feed additive against carbapenem-resistant gram-negative bacteria which includes ADK protein as an active ingredient.

The present invention also provides a pharmaceutical composition or a food composition for the prevention or treatment of infectious diseases caused by carbapenem-resistant gram-negative bacteria, the composition including ADK protein as an active ingredient.

Advantageous Effects

According to the present invention, ADK protein derived from *Mycobacterium tuberculosis* has excellent antibacterial activity against carbapenem-resistant gram-negative bacteria, and thus may be usefully used in a variety of fields as an antibacterial composition.

DESCRIPTION OF DRAWINGS

The FIGURE is an image showing sodium dodecyl sulfate-polyacrylamide gel electrophoresis (SDS-PAGE) analysis results of recombinant ADK protein.

BEST MODE

Hereinafter, the present invention will be described in more detail.

The present invention provides an antibacterial composition against carbapenem-resistant gram-negative bacteria which includes ADK protein as an active ingredient.

The term "antibacterial" or "antibacterial activity" as used herein refers to a property of resisting microorganisms such as bacteria or fungi, more particularly, refers to properties of antibiotics and the like which inhibit the growth or proliferation of bacteria.

The term "antibacterial composition" as used herein refers to a composition having the activity of inhibiting the growth and development of microorganisms such as bacteria or fungi, and may include all forms used in a variety of fields requiring antimicrobial effects, for example, drugs, quasi-drugs, food additives, feed additives, or the like. In particular, the antibacterial composition may be used in products directly associated with microorganisms, such as: antibiotics or contamination inhibitors in the medical field; foods for antiseptic or antimicrobial purposes; in agriculture for antimicrobial, bactericidal, or antiseptic purposes; cosmetics or daily supplies to inhibit dandruff, prevent athlete's foot, or inhibit the odor of the armpits, or for anti-acne purposes; and the like, or detergents for cleaning, detergents for washing dishes, or the like for antiseptic, antimicrobial, or bactericidal purposes, but the present invention is not limited to the above purposes.

The ADK protein of the present invention is derived from *Mycobacterium tuberculosis*, may preferably have an amino acid sequence represented by SEQ ID NO: 1, may be encoded by a base sequence represented by SEQ ID NO: 2, and includes functional equivalents of the ADK protein. The term "functional equivalents" as used herein refers to proteins that have sequence homology of at least 70%, preferably, at least 80%, more preferably, at least 90%, most preferably, at least 95% with the amino acid sequence of SEQ ID NO: 1 as a result of the addition, substitution or deletion of amino acids and exhibit substantially the same physiological activity as that of the protein having the amino acid sequence of SEQ ID NO: 1 or the protein encoded by the base sequence of SEQ ID NO: 2.

The ADK protein of the present invention includes both proteins having natural amino acid sequences thereof and amino acid sequence variants thereof. The variants of the ADK protein refer to proteins having different sequences by deletion, insertion, or non-conservative or conservative substitution of an ADK natural amino acid sequence and one or more amino acid residues, or a combination thereof. Amino acid exchange in proteins and peptides that does not overall alter the activity of molecules is known in the art. The ADK protein or the variants thereof may be naturally extracted or synthesized (Merrifield, J. Amer. Chem. Soc. 85:2149-2156, 1963) or may be prepared by gene recombination based on a DNA sequence (Sambrook et al, Molecular Cloning, Cold Spring Harbor Laboratory Press, New York, USA, $2^{nd}$ Edition, 1989).

The ADK protein of the present invention may be encoded by a base sequence of SEQ ID NO: 2, and variants capable of performing functionally the same action as that of the nucleotide are included within the scope of the present invention.

The term "gram-negative bacteria" as used herein refers to bacteria stained red by Gram staining and, generally, these bacteria have strong resistance to pigments and surfactants. The gram-negative bacteria of the present invention include all types of gram-negative bacteria containing endotoxins, and examples thereof include, but are not limited to, bacteria belonging to the genus *Escherichia*, the genus *Pseudomonas*, the genus *Acinetobacter*, the genus *Salmonella*, the genus *Klebsiella*, the genus *Neisseria*, the genus *Enterobacter*, the genus *Shigella*, the genus *Moraxella*, the genus *Helicobacter*, the genus *Stenotrophomonas*, the genus *Bdellovibrio*, and the genus *Legionella*. In particular, examples of these gram-negative bacteria include, but are not limited to, *Escherichia coli, Pseudomonas aeruginosa, Pseudomonas fluorescens, Pseudomonas putida, Pseudomonas chlororaphis, Pseudomonas pertucinogena, Pseudomonas stutzeri, Pseudomonas syringae, Acinetobacter baumannii, Acinetobacter lwoffii, Acinetobacter calcoaceticus, Acinetobacter haemolyticus, Salmonella enterica, Salmonella bongori, Salmonella enteritidis, Salmonella typhimurium, Salmonella gallinarum, Salmonella pullorum, Salmonella mbandaka, Salmonella choleraesuls, Salmonella thompson, Salmonella infantis, Salmonella derby, Klebsiella pneumonia, Klebsiella granulomatis, Klebsiella oxytoca, Klebsiella terrigena, Neisseria gonorrhoeae, Neisseria meningitidis, Enterobacter aerogenes, Enterobacter cloacae, Shigella boydii, Shigella dysenteriae, Shigella flexneri, Shigella sonnei, Moraxella catarrhalis, Moraxella lacunata, Moraxella bovis, Helicobacter pylori, Helicobacter heilmannii, Helicobacter felis, Helicobacter mustelae, Helicobacter fenelliae, Helicobacter rappini, Helicobacter hepaticus, Helicobacter bilis, Helicobacter pullorum, Stenotrophomonas maltophilia, Stenotrophomonas nitritireducens, Bdellovibrio bacteriovorus, Legionella pneumophila, Legionella anisa, Legionella birminghamensis, Legionella bozemanii, Legionella cincinnatiensis, Legionella dumoffii, Legionella feeleii, Legionella gormanii, Legionella hackeliae, Legionella israelensis, Legionella jordanis, Legionella lansingensis, Legionella longbeachae, Legionella maceachernii, Legionella micdadei, Legionella oakridgensis, Legionella sainthelensi, Legionella tucsonensis*, and *Legionella wadsworthii*.

The term "carbapenem" as used herein refers to one type of β-lactam antibiotic which has a structure represented by Formula 1 below:

<Formula 1> 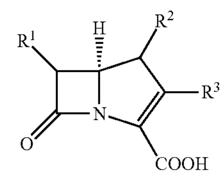 wherein, in Formula 1, each of $R_1$ and $R_2$ is independently H, a $C_1$-$C_{10}$ alkyl, or a $C_1$-$C_{10}$ alkyl substituted with a hydroxyl group, and $R_3$ is H, —O—$R_4$, or —S—$R_4$, wherein $R_4$ is a N-substituted or C-substituted amine or pyrrolidine.

Examples of carbapenem antibiotics include, but are not limited to, imipenem, meropenem, ertapenem, doripenem, panipenem/betamipron, biapenem, razupenem, tebipenem, lenapenem, and tomopenem.

Structures of imipenem, panipenem, meropenem, ertapenem, and doripenem, which are representative carbapenem antibiotics, are shown in Formulae 2, 3, 4, 5, and 6, respectively:

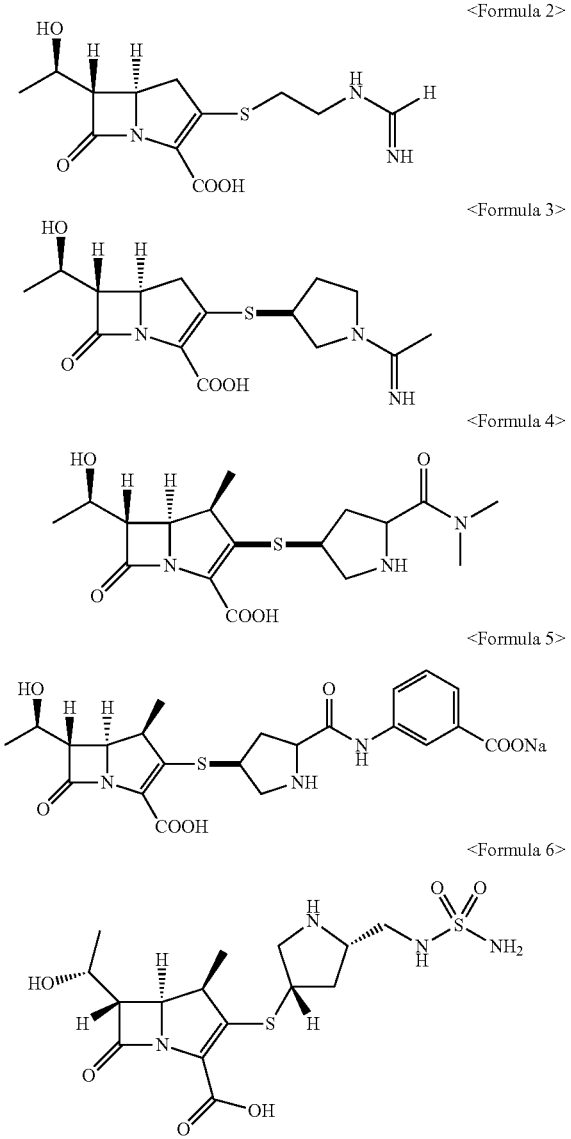
<Formula 2>
<Formula 3>
<Formula 4>
<Formula 5>
<Formula 6>

The ADK protein derived from *Mycobacterium tuberculosis*, according to the present invention, has excellent antimicrobial activity against carbapenem-resistant gram-negative bacteria, and thus may be usefully used as an antibacterial composition in a variety of fields, i.e., quasi-drugs, food additives, feed additives, and the like.

The present invention also provides an antibacterial quasi-drug, an antibacterial food additive, or an antibacterial feed additive against carbapenem-resistant gram-negative bacteria which includes ADK protein as an active ingredient.

The present invention also provides a composition for the prevention or treatment of infectious diseases caused by carbapenem-resistant gram-negative bacteria which includes ADK protein as an active ingredient.

The composition includes a pharmaceutical composition or a food composition.

The present invention also provides a method of preventing or treating infectious diseases caused by carbapenem-resistant gram-negative bacteria, the method including administering ADK protein to an individual.

The ADK protein of the present invention selectively exhibits excellent antimicrobial activity against carbapenem-resistant gram-negative bacteria, and thus a composition including the same may be usefully used in the prevention or treatment of infectious diseases caused by carbapenem-resistant gram-negative bacteria.

The term "infectious diseases" as used herein refers to illnesses caused by disease-causing pathogenic microorganisms, such as viruses, bacteria, fungi, and parasites through propagation and intrusion into animals or humans, and refers to all infectious diseases caused by carbapenem-resistant gram-negative bacteria in accordance with the objects of the present invention. For example, the infectious diseases of the present invention may be respiratory diseases, gastrointestinal diseases, inflammatory diseases, and the like. In particular, examples of the infectious diseases include, but are not limited to, pneumonia, peritonitis, meningitis, wound infections, osteoarthritis, cholecystitis, urinary tract infections, cerebromeningitis, endocarditis, myocarditis, pericarditis, arthritis, pharyngitis, gonorrhea, bacillary dysentery, enteritis, conjunctivitis, gastritis, tympanitis, cystitis, lymphangitis, and septicemia.

The term "prevention" as used herein means all actions that inhibit infectious diseases or delay the onset thereof via administration of the composition. The term "treatment" as used herein means all actions that alleviate or beneficially change symptoms due to infectious diseases via administration of the composition.

The pharmaceutical composition of the present invention may further include a commonly used suitable carrier, excipient or diluent. Examples of the carrier, the excipient, or the diluent that may be included in the pharmaceutical composition of the present invention include, but are not limited to, lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil.

The pharmaceutical composition of the present invention may be administered in oral or parenteral forms according to a general method, and is formulated using generally used diluents or excipients such as fillers, extenders, binders, wetting agents, disintegrating agents, surfactants, and the like. Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used. Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a flavoring agent, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate. Examples of suppository bases include Witepsol, Macrogol, Tween 61, cacao butter, laurin, glycerogelatin, and the like.

The term "administration" as used herein refers to supply of the pharmaceutical composition of the present invention to an individual by using an appropriate method.

A suitable dose of the pharmaceutical composition of the present invention may vary depending on conditions and body weights of patients, severity of disease, types of drugs, administration route, and administration time, but may be appropriately selected by those of ordinary skill in the art. To obtain desired effects, the pharmaceutical composition of the present invention may be administered in an amount of 0.001 mg/kg to 1000 mg/kg daily. The pharmaceutical composition may be administered once or multiple times a day. The dosage is not intended to limit the scope of the present invention in any way.

The pharmaceutical composition of the present invention may be administered to an individual via a variety of routes. All administration methods may be expected, for example, oral injection, rectal or intravenous injection, muscular injection, subcutaneous injection, intrauterine epidural injection, and intracerebroventricular injection. However, for oral administration, since a protein is digested, an oral composition may be formulated such that active ingredients are coated, or formulated to be protected from being decomposed in the stomach. The composition of the present invention may be administered preferably in the form of an injection.

The pharmaceutical composition according to the present invention may further include one or more known substances having antimicrobial activity in addition to the ADK protein.

In the present invention, the food composition may be preferably in the form of health functional foods.

In the present invention, the health functional food refers to a group of foods having added values provided by a physical, biochemical, or biotechnological method so that the corresponding food imparts or exhibits intended functions suitable for specific applications, or a processed food designed such that a composition of the food sufficiently imparts, in the body, body modulation functions regarding biological defense rhythm control, disease prevention and recovery, and the like.

The health functional food may include sitologically acceptable food supplement additives, and may further include suitable carriers, excipients, and diluents commonly used to prepare a health functional food.

When the food composition of the present invention is used as a food additive, the composition may be appropriately used alone or in combination with other foods or food ingredients according to a commonly used method. A mixing amount of active ingredients may be appropriately determined according to the purpose of use (prevention, health or medical treatment). In general, in preparation of foods or beverages, the composition of the present invention may be added in an amount of 15 wt % or less, preferably, 10 wt % or less, with respect to raw materials. However, when ingested for a long period of time for health and hygiene purposes or for health control purposes, the food composition may be included in an amount in or less than the above ranges of amounts. The composition has no problem in terms of safety, and thus may also be used in an amount in or greater than the above ranges of amounts.

In addition to the above-listed ingredients, the food composition of the present invention may include various nutritional supplements, vitamins, electrolytes, flavors, colorants, pectic acid and salts thereof, alginic acid and salts thereof, organic acids, a protective colloid thickener, a pH adjusting agent, a stabilizer, a preservative, glycerin, alcohols, a carbonating agent used in carbonated beverages, and the like. In addition, the food composition of the present invention may include flesh for the preparation of natural fruit juice, fruit juice beverages, and vegetable beverages. These ingredients may be used alone or in combination. The proportion of these additives is not very important, but the amounts of the additives are generally selected from 0.01 parts by weight to 0.1 parts by weight based on 100 parts by weight of the composition of the present invention.

Hereinafter, exemplary examples will be described to aid in understanding of the present invention. However, these examples are provided only to more easily understand the present invention and are not intended to limit the scope of the present invention.

Example 1. Cloning of Recombinant ADK (Rv0733)

The ADK (Rv0733) region was amplified by PCR using genomic DNA of *Mycobacterium tuberculosis* H37Rv (ATCC 27294) as a template (primer: 5'-CATATGAGAGTTTTGTTGCTGGGACCG-3' (SEQ ID NO: 3) and 5'-AAGCTTCTTTCCCAGAGCCCGCAACGC-3' (SEQ ID NO: 4)). The isolated PCR product was digested with NdeI and HindIII enzymes and inserted into the expression vector pET22b. *E. coli* BL21 transformed with the vector pET22b into which the ADK gene was inserted was cultured in an LB medium (containing 100 µg/ml of ampicillin) at 37° C. for 12 hours. Subsequently, 1 mM isopropyl-D-thiogalactopyranoside (IPTG) was added thereto, followed by culturing for 6 hours, and the cells were lysed with a lysis buffer (containing 1M DTT, lysozyme, and PMSF). A recombinant protein was purified using nickel-nitrilotriacetic acid agarose (Ni-NTA, Invitrogen, Carlsbad, Calif., USA) in accordance with a method of the manufacturer. Finally, the purified recombinant ADK protein was identified by SDS-PAGE. The results thereof are illustrated in the FIGURE.

Example 2. Identification of Carbapenem-Resistant Gram-Negative Bacteria

*Acinetobacter baumannii* KUMC.2014.90 and KUMC.2014.91 strains were isolated from blood samples of patients of the Division of Infectious Diseases of Korea University. To identify the resistance of the strains to antibiotics, a VITEK II system, which is an automated device, was primarily used and, as a result, it was confirmed that the strains have resistance to all carbapenem-based antibiotics, i.e., imipenem, meropenem, ertapenem, and the like (confirmed results values of R>32). Secondarily, the resistance of the strains to imipenem and meropenem, which are carbapenem-based antibiotics, was reconfirmed using a liquid medium microdilution method (confirmed result values of greater than 128 µg/ml).

Experimental Example 1. Verify Antibacterial Activity of ADK Protein Against Carbapenem-Resistant Gram-Negative Bacteria To verify the antibacterial activity of the recombinant ADK protein obtained in Example 1 against the carbapenem-resistant *Acinetobacter baumannii* (KUMC.2014.90 and KUMC.2014.91 strains) obtained in Example 2, Rezazurin assay was performed according to a conventionally known method to measure a minimum inhibitory concentration (MIC) and a minimum bactericidal concentration (MBC) for the carbapenem-resistant *Acinetobacter baumannii* strains. As a control, *Acinetobacter bau-*

*mannii*, which is a normal strain, was used. Experimental results are shown in Table 1 below.

TABLE 1

| Organisms and antimicrobial agent | Testing range | MIC (μg/ml) 50% | MIC (μg/ml) 80% | MBC (μg/ml) |
|---|---|---|---|---|
| *Acinetobacter baumannii* | | | | |
| Ampicillin | 0.45~500 | <31.3 | <62.5 | <62.5 |
| Rukasyn | 0.45~500 | <1 | <2 | <3.9 |
| Cravit | 0.45~500 | <0.5 | <1 | <1 |
| Prepenem | 0.45~500 | <0.5 | <1 | <1 |
| Adk | 0.45~500 | <3.9 | <7.8 | <7.8 |
| *Acinetobacter baumannii* (KUMC.2014.90) | | | | |
| Ampicillin | 0.45~500 | No effect | No effect | No effect |
| Rukasyn | 0.45~500 | <15.6 | <31.3 | <31.3 |
| Cravit | 0.45~500 | <7.8 | <15.6 | <15.6 |
| Prepenem | 0.45~500 | <31.3 | <62.5 | <62.5 |
| Adk | 0.45~500 | <1 | <2 | <2 |
| *Acinetobacter baumannii* (KUMC.2014.91) | | | | |
| Ampicillin | 0.45~500 | No effect | No effect | No effect |
| Rukasyn | 0.45~500 | <15.6 | <31.3 | <31.3 |
| Cravit | 0.45~500 | <7.8 | <15.6 | <15.6 |
| Prepenem | 0.45~500 | <31.3 | <62.5 | <62.5 |
| Adk | 0.45~500 | <3.9 | <7.8 | <7.8 |

As shown in Table 1, as a result of calculating 50% and 80% inhibitory concentrations assuming that result values of wells not treated with antibiotics and ADK protein were 100%, it was confirmed that antibiotics (i.e., ampicillin, rukasyn, cravit, and prepenem) inhibited the growth of *Acinetobacter baumannii*, which is a normal strain, while being unable to inhibit the growth of the carbapenem-resistant *Acinetobacter baumannii* (KUMC.2014.90 and KUMC.2014.91 strains). In contrast, it was confirmed that the ADK protein significantly inhibited the growth of both *Acinetobacter baumannii*, which is a normal strain, and the two types of carbapenem-resistant *Acinetobacter baumannii* (KUMC.2014.90 and KUMC.2014.91 strains).

From the above-described experimental results, it was confirmed that ADK protein derived from *Mycobacterium tuberculosis*, according to the present invention, had excellent antimicrobial activity against carbapenem-resistant gram-negative bacteria.

Hereinafter, the pharmaceutical composition and food composition of the present invention will be described with reference to the following preparation examples. However, these examples are provided only for illustrative purposes and are not intended to limit the scope of the present invention.

Preparation Example 1. Preparation of Pharmaceutical Composition

1-1. Preparation of Powder

| | |
|---|---|
| ADK protein | 2 g |
| Lactose | 1 g |

The above ingredients were mixed and airtight packages were filled therewith, thereby completing the preparation of powder.

1-2. Preparation of Tablets

| | |
|---|---|
| ADK protein | 100 mg |
| Corn starch | 100 mg |
| Lactose | 100 mg |
| Magnesium stearate | 2 mg |

The above ingredients were mixed, and then tablets were prepared according to a general method of preparing tablets.

1-3. Preparation of Capsules

| | |
|---|---|
| ADK protein | 100 mg |
| Corn starch | 100 mg |
| Lactose | 100 mg |
| Magnesium stearate | 2 mg |

The above ingredients were mixed, and then gelatin capsules were filled therewith according to a general method of preparing capsules, thereby completing the preparation of capsules.

Preparation Example 2. Preparation of Food Composition

2-1. Preparation of Health Food

| | |
|---|---|
| ADK protein | 100 mg |
| Vitamin mixture | appropriate amount |
| Vitamin A acetate | 70 g |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 g |
| Vitamin C | 10 mg |
| Biotin | 10 g |
| Nicotinamide | 1.7 mg |
| Folic acid | 50 g |
| Calcium pantothenate | 0.5 mg |
| Mineral mixture | appropriate amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The vitamin mixture and the mineral mixture were composed of a mixture of relatively suitable ingredients for health foods as an exemplary embodiment, but the mixing ratio may be arbitrarily modified, and the above ingredients were mixed according to a general method of preparing health foods and prepared into granules, and may be used in the preparation of a health food composition according to a general method.

The invention claimed is:

1. A method of treating an infectious disease caused by carbapenem-resistant gram-negative bacteria comprising administering a composition comprising adenylate kinase (ADK) protein as an active ingredient to a subject in need thereof.

2. The method of claim 1, wherein the ADK protein is derived from *Mycobacterium tuberculosis*.

3. The method of claim 1, wherein the ADK protein is represented by SEQ ID NO: 1.

4. The method of claim 1, wherein the ADK protein is encoded by a base sequence represented by SEQ ID NO: 2.

5. The method of claim 1, wherein the infectious disease caused by carbapenem-resistant gram-negative bacteria is selected from the group consisting of pneumonia, peritonitis, meningitis, wound infections, osteoarthritis, cholecystitis, urinary tract infections, cerebromeningitis, endocarditis, myocarditis, pericarditis, arthritis, pharyngitis, gonorrhea, bacillary dysentery, enteritis, conjunctivitis, gastritis, tympanitis, cystitis, lymphangitis, and septicemia.

6. The method of claim 1, wherein the composition is an antibacterial quasi-drug composition, antibacterial food additive, antibacterial feed additive composition, pharmaceutical composition or food composition.

7. A method of alleviating an infectious disease caused by carbapenem-resistant gram-negative bacteria comprising administering a composition comprising adenylate kinase (ADK) protein as an active ingredient to a subject in need thereof.

8. The method of claim 7, wherein the composition is an antibacterial quasi-drug composition, antibacterial food additive, antibacterial feed additive composition, pharmaceutical composition or food composition.

* * * * *

SEQUENCE LISTING

<160> NUMBER OF SEQ ID NOS: 4

<210> SEQ ID NO 1
<211> LENGTH: 181
<212> TYPE: PRT
<213> ORGANISM: Mycobacterium tuberculosis

<400> SEQUENCE: 1

Met Arg Val Leu Leu Gly Pro Pro Gly Ala Gly Lys Gly Thr Gln
1               5                   10                  15

Ala Val Lys Leu Ala Glu Lys Leu Gly Ile Pro Gln Ile Ser Thr Gly
            20                  25                  30

Glu Leu Phe Arg Arg Asn Ile Glu Glu Gly Thr Lys Leu Gly Val Glu
        35                  40                  45

Ala Lys Arg Tyr Leu Asp Ala Gly Asp Leu Val Pro Ser Asp Leu Thr
    50                  55                  60

Asn Glu Leu Val Asp Asp Arg Leu Asn Asn Pro Asp Ala Ala Asn Gly
65                  70                  75                  80

Phe Ile Leu Asp Gly Tyr Pro Arg Ser Val Glu Gln Ala Lys Ala Leu
                85                  90                  95

His Glu Met Leu Glu Arg Arg Gly Thr Asp Ile Asp Ala Val Leu Glu
            100                 105                 110

Phe Arg Val Ser Glu Glu Val Leu Glu Arg Leu Lys Gly Arg Gly
        115                 120                 125

Arg Ala Asp Asp Thr Asp Asp Val Ile Leu Asn Arg Met Lys Val Tyr
130                 135                 140

Arg Asp Glu Thr Ala Pro Leu Leu Glu Tyr Tyr Arg Asp Gln Leu Lys
145                 150                 155                 160

Thr Val Asp Ala Val Gly Thr Met Asp Glu Val Phe Ala Arg Ala Leu
                165                 170                 175

Arg Ala Leu Gly Lys
            180

<210> SEQ ID NO 2
<211> LENGTH: 546
<212> TYPE: DNA
<213> ORGANISM: Mycobacterium tuberculosis

<400> SEQUENCE: 2
gtgagagttt tgttgctggg accgcccggg gcgggcaagg ggacgcaggc ggtgaagctg      60
gccgagaagc tcgggatccc gcagatctcc accggcgaac tcttccggcg caacatcgaa     120
gagggcacca agctcggcgt ggaagccaaa cgctacttgg atgccggtga cttggtgccg     180
tccgacttga ccaatgaact cgtcgacgac cggctgaaca atccggacgc ggccaacgga     240
ttcatcttgg atggctatcc acgctcggtc gagcaggcca aggcgcttca cgagatgctc     300
gaacgccggg gaccgacat cgacgcggtg ctggagtttc gtgtgtccga ggaggtgttg      360
ttggagcgac tcaaggggcg tggccgcgcc gacgacaccg acgacgtcat cctcaaccgg     420
atgaaggtct accgcgacga gaccgcgccg ctgctggagt actaccgcga ccaattgaag     480
accgtcgacg ccgtcggcac catggacgag gtgttcgccc gtgcgttgcg ggctctggga     540
aagtag                                                                546

<210> SEQ ID NO 3
<211> LENGTH: 27
<212> TYPE: DNA
<213> ORGANISM: Artificial Sequence -continued

```
<220> FEATURE:
<223> OTHER INFORMATION: F Primer

<400> SEQUENCE: 3
catatgagag ttttgttgct gggaccg                                          27

<210> SEQ ID NO 4
<211> LENGTH: 27
<212> TYPE: DNA
<213> ORGANISM: Artificial Sequence
<220> FEATURE:
<223> OTHER INFORMATION: R Primer

<400> SEQUENCE: 4
aagcttcttt cccagagccc gcaacgc                                          27
```